(12) United States Patent
Egert et al.

(10) Patent No.: US 7,256,006 B2
(45) Date of Patent: Aug. 14, 2007

(54) METHOD FOR DETERMINING THE INFLUENCE OF A TEST SUBSTANCE ON THE HEART ACTIVITY OF A VERTEBRATE

(75) Inventors: Ulrich Egert, Freiburg (DE);
Karl-Heinz Boven, Tübingen (DE);
Andreas Möller, Tübingen (DE);
Kathrin Banach, Oak Park, IL (US)

(73) Assignee: Multi Channel Systems MCS GmbH, Reutlingen (DE)

(*) Notice: Subject to any disclaimer, the term of this patent is extended or adjusted under 35 U.S.C. 154(b) by 0 days.

(21) Appl. No.: 11/191,397

(22) Filed: Jul. 28, 2005

(65) Prior Publication Data

US 2006/0172277 A1 Aug. 3, 2006

Related U.S. Application Data

(63) Continuation of application No. PCT/EP2004/000717, filed on Jan. 28, 2004.

(30) Foreign Application Priority Data

Jan. 29, 2003 (DE) ................. 103 03 544

(51) Int. Cl.
*G01N 33/567* (2006.01)
(52) U.S. Cl. .................................. 435/7.21
(58) Field of Classification Search ............... None
See application file for complete search history.

(56) References Cited

OTHER PUBLICATIONS

Netzer et al. Drug Discovery Today (DDT) 2001;6(2):78-84.*
Nimodipine—webpage printout-Wikipedia—1 page.*
Bucher, Biosensors and Bioelectronics (2001) 16(3):205-210.
Denyer et al., Medical and Biological Engineering and Computing (1998) 36:638-644.
Duffy et al., Society for Neuroscience Abstracts (2001) 27:1766.
Igelmund et al., Pfluegers Archiv. European Journal of Physiology (1999) 437:669-679.
International Search Report for PCT/EP2004/000717, mailed on Jun. 24, 2004, 3 pages.
Israel et al., Am J. Physiology (1984) 247:H669-H674.
Lengyel et al., Br. J. Pharmacol. (2001) 132(1):101-110 (Abstract Only).
Meiry et al., Journal of Cardiovascular Electrophysiology (2001) 12:1269-1277.
Stett et al., Analytical and Bioanalytical Chemistry (2003) 1-21.

* cited by examiner

*Primary Examiner*—Ralph Gitomer
*Assistant Examiner*—Bin Shen
(74) *Attorney, Agent, or Firm*—Morrison & Foerster LLP

(57) ABSTRACT

In a method for determining the influence of a test substance on the heart activity of a vertebrate the following steps are performed:

a) preparation of a culture of spontaneously active heart cells of the vertebrate, b) extracellular measurement of electrophysiological data of the heart cells from step a), c) addition of the test substance to the culture from step a), d) repetition of the measurement from step b), and e) comparison of data from step b) and step d).

15 Claims, 4 Drawing Sheets

METHOD FOR DETERMINING THE INFLUENCE OF A TEST SUBSTANCE ON THE HEART ACTIVITY OF A VERTEBRATE

Related Application

This is a continuation application of International Patent Application PCT/EP2004/000717, filed Jan. 28, 2004, designating the United States and published as WO 2004/067734 A1, which claims priority to German Application No. 103 03 544.3, filed Jan. 29, 2003. The disclosures of the above-referenced applications are herein incorporated by reference in their entirety.

BACKGROUND OF THE INVENTION

1. Field of the Invention

The present invention relates to a method for determining the influence of a test substance on the heart activity of a vertebrate, in particular on the interval between ventricular depolarization and repolarization.

2. Related Prior Art

It has long been known that many substances with which animals and humans come into contact may have an influence on heart activity. These substances can generally be environmental factors which are absorbed by breathing or through the skin or in food, or intentionally administered pharmaceutical substances and cosmetic products. In the context of the present application, these substances are generally referred to as "substances" or "test substances".

To protect livestock animals, domestic animals and, in particular, human beings from the harmful or damaging influence of such substances, not only are the toxicity and the desired action of these substances tested, but increasingly also their undesired influence on heart activity, before said substances are released for use.

In addition, however, there is also a need to test substances already in use, in particular approved medicaments or those being used in clinical trials, in order to ascertain their influence on heart activity. In the case of medicines in particular, undesired side effects on heart rate activity often arise which are not detected in the context of the clinical trials conducted for approval of these medicines or in the preliminary stages of such clinical trials. This leads to a potential danger to persons participating in clinical studies in particular, and to all patients in general.

Such undesired side effects may only become apparent as harmful for example after pro-longed administration, in combination with other substances, or in the presence of risk factors, for example hypokalemia, or structural heart disease, so that they cannot be reliably detected either in the preliminary phases of or during the conduct of clinical trials and studies.

In the context of clinical trials and studies, the influence of substances on heart activity can be determined by what is called electrocardiography, that is to say by recording the ventricular stimulus conduction in the heart in the course of heart activity, the time course being plotted as a tracing, a so-called electrocardiogram. The tracings represent the sum of the intensities and directions of the electrical potentials in the individual myocardial and nerve fibres, and they are recorded by leads assigned in different spatial configurations with respect to the heart, for example on the extremities.

An electrocardiogram is divided into different elements which can be assigned to different physiological processes. The P wave records the excitation of the atrium, and it is followed by the isoelectric PQ segment which records the conduction time of the excitation to the ventricles. The QRS complex corresponds to the ventricular excitation; this is followed by the ST segment, which in turn is followed by the T wave which corresponds to the ventricular repolarization. From the changes in the segment duration and the shape of the elements in the recorded tracings, it is possible to draw important conclusions regarding the heart.

An important variable here is the QT interval, that is to say the time from the start of the QRS complex to the end of the T wave, reflecting the overall electrical action of the ventricle. This QT interval is therefore a measure of the duration of the ventricular depolarization and repolarization.

It is known that a change in the QT interval leads to increased health risks, particularly as a result of rhythm disturbances. For example, a prolongation of the QT interval leads to an increased risk of ventricular tachycardia and fatal arrhythmia. This change in the QT interval may be congenital or may have been acquired as a result of disease or ingestion of harmful substances.

Numerous medicaments are known with which a desired change in the QT interval can be effected in order to counteract pathological changes. On the other hand, there are many substances which have an undesired influence on the QT interval which in many cases goes unrecognized or cannot be detected in conventional clinical studies.

However, even if the influence of substances on heart activity and the associated side effects, for example QT prolongation, could be reliably and conclusively determined with the aid of electrocardiography in the context of clinical studies, the conduct of such studies nevertheless constitutes an unacceptable risk to those participating in these studies and investigations. Quite apart from the ethical problems surrounding the conduct of tests on animals, these tests in the final analysis are not purposeful because there is a limit to the extent to which data from animal tests can be transposed to humans.

In addition, not only would carrying out clinical studies or animal experiments to test the many substances already on the market for their influence on heart activity be associated with high costs, it would also take a considerable time before each particular study was concluded.

SUMMARY OF THE INVENTION

In view of the above, one object of the present invention is to make available a method of the aforementioned type which can be performed quickly and inexpensively and without the need for tests on humans or animals.

According to the invention, this object is achieved by a method of the aforementioned type which comprises the following steps:
  a) preparation of a culture of spontaneously active heart cells of the vertebrate,
  b) extracellular measurement of electrophysiological data of the heart cells from step a),
  c) addition of the test substance to the culture from step a),
  d) repetition of the measurement from step b), and
  e) comparison of data from step b) and step d).

The object of the invention is achieved in full in this way.

The inventors of the present application have in fact found that electrophysiological data from extracellular recordings from cultured heart cells permit conclusions on heart activity which conventionally can be obtained only from an ECG lead.

This finding is all the more astonishing given that, for example, ventricular repolarization, which crucially defines heart activity, is a complex physiological process. It is the result of the interaction of many ion channels and transporters whose activities under physiological conditions are very much dependent on one another and are determined, for example, by intra-cellular and extracellular ion concentrations, membrane potential, heart rate, metabolism, etc.

Against this background, it was not to be expected that in vitro measurements can be brought into any reliable correlation with the complex in vivo conditions and permit conclusions regarding the influence of substances on heart activity.

However, the inventors have not taken what is, despite the doubtful correlation, the per-haps obvious course of determining the action potential of heart cells by intracellular measurements and drawing conclusions from these about heart activity. Instead, they have been able to show that extracellular measurements of the field potential of heart cells in culture provide evidence regarding the in vivo conditions.

This evidence is of an essentially qualitative nature and indicates whether and if so what influence the tested substance has on heart activity, particularly on the QT interval. It therefore represents a kind of pre-screening for determining whether the test substance has to be further evaluated if appropriate in clinical studies or whether it is harmless with respect to heart activity. The qualitative evidence on whether a QT prolongation or shortening is to be reckoned with also provides important information on the design and evaluation of clinical studies and on the nature of the side effects that may be expected, particularly also in connection with previous diseases or existing medication. By means of an in vitro test which can be performed easily, quickly and inexpensively compared to human or animal experiments, the safety of test subjects and patients can thus be significantly increased.

The measurements can be carried out on individual heart cells, on aggregates of heart cells or on tissue composites or aggregates, and the cells can be native heart cells, for example from biopsy material or from clinical material, or, alternatively, cell lines can also be used. The important point is merely that the culture contains spontaneously beating heart cells or similar, for example cells derived from stem cells.

In this way it is possible to draw general conclusions concerning the influence of the test substance on heart activity in general and also specific conclusions concerning the influence in individual patients. Thus, it is possible not just to evaluate the respective substance in general, but also to investigate an individual patient to determine how he reacts to certain substances, so that the method according to the invention can be employed also in the context of a diagnostic procedure or in the run-up to a therapeutic procedure.

The method can also be used to select or produce a specifically tailored medicament for a specific patient, taking into account his physiological status and his particular disease. To do so, heart cells from the patient himself are used so that it is possible to carry out an in vitro check as to how the particular patient reacts to the substance. It is thus possible to check, for example prior to a course of medication, whether a substance with known but rare side effects can be administered to a specific patient. The heart cells in this case derive either from biopsies or from surgical interventions, balloon dilations, etc., or are differentiated from the patient's stem cells.

Therefore, according to another object, the invention is directed to a method for treating a human individual or an animal, comprising the steps of:
 a) selecting a test substance suitable for said treatment,
 b) providing heart cells of said human individual or animal,
 c) determining the influence of said test substance on the activity of said heart cells, by the method of anyone of claims 1-16,
 d) preparing a pharmaceutical composition containing said test substance in case said influence on the heart activity is admissible.

All in all, the method according the invention can be performed inexpensively and quickly compared to clinical studies. Prior to tests on humans or animals, it permits determination of potential dangers to the subjects and a better design and better interpretation of clinical studies.

The method according to the invention thus makes it easier to determine the potential danger to and protection of subjects and patients in connection with new and with known medicines, and the investigation of environmental factors of all kinds, including in veterinary medicine or in connection with work place safety, and in the cosmetics industry. It provides information on whether a substance is to be classified as reasonably safe in respect of its influence on heart activity, in particular on the QT interval, or whether particular caution is required in administering it and whether further or special clinical studies may be necessary.

The measurements were carried out in the first instance with so-called MEAs (multi-electrode arrays), as are marketed by the Applicant, for example as the MEA60 system. In these devices, a number of microelectrodes are integrated on a substrate, and heart cells are cultured on these. The microelectrodes are used to record the field potentials at different sites of the tissue culture, so that, in addition to the time course of the field potential at a measurement site, it was also possible to investigate the spatial propagation of the signals. Initial measurement results showed that it is not necessary to carry out measurements at different sites in a tissue culture or on individual cells in order to obtain reliable evidence concerning the time course of the field potential in the culture and to draw conclusions on the influence of the tested substance on heart activity. Rather, it is sufficient to use a measurement electrode or microelectrode which is completely covered by a cell or by an electrically coupled cell aggregate.

The measurements are therefore preferably carried out with the aid of a device for extracellular recording of electrophysiological data, as is described for example in DE 197 12 309. With this device it is possible to carry out measurements on separate individual cells or cell composites and aggregates, which are preferably present in microcuvettes of suitable dimensions arranged in a support plate. The cells or tissue composites are cultured in the microcuvettes at the bottoms of which there is in each case at least one measurement electrode with which the field potential can be measured on cells in the respective microcuvette.

It is also possible to use a type of microtitre plate with, for example, 96 cuvettes or wells in the standard grid, a measurement electrode being arranged at the bottom of each well, and a reference electrode additionally being arranged in the well. Cell composites, that is to say tissue cultures or electrically coupled aggregates of heart cells, are incubated in the wells; they cover the measurement electrode and their field potential is recorded.

In the various microcuvettes or wells of these devices, either heart cells of different origin can be cultured in order to investigate the influence of a substance on the different heart cells, or alternatively heart cells of a single origin are cultured and the effect of a different substance is investigated in each microcuvette. Of course, a combination of the two procedures can be chosen in which both heart cells of different origin and also different substances are tested simultaneously on a support plate with a large number of microcuvettes. In addition to the test substance or substances, reference substances can also be tested, in order for example to calibrate the measurement results.

Against this background, the present invention also concerns the use of a device for extracellular recording of electrophysiological data, for example an MEA or a support plate with microcuvettes in each of which at least one measurement electrode is arranged, in the aforementioned method.

In steps b) and d), the time course of the field potential (FP) of the culture is preferably measured, and it is further preferable for at least one parameter, FPdur and/or FPrise, to be calculated from the FP time course and compared, the change in this parameter by addition of the test substance to the culture being a measure of the influence of the substance on heart activity.

In active or beating heart cells, the field potential showed a pattern recurring in the heart beat rhythm consisting of a first minimum and a last maximum, and in which it was possible for a further maximum to precede in each case the first minimum and the last maximum. The time interval FPdur between the first minimum and the last maximum proved, in initial experiments by the inventors, to be a parameter whose change as a result of addition of a test substance is comparable to the change in the QT interval arising when this substance is administered to a patient. A substance known to cause a QT prolongation increased the parameter FPdur, while another substance known to cause a QT shortening reduced FPdur.

A further relevant parameter of the FP wave shape proved to be the duration of the falling flank in the FP wave shape from the zero line to the first minimum, which is characterized by a parameter FPrise. FPrise is calculated as the duration between reaching, for example, 10% of the first minimum and reaching the first minimum. In the experience of the inventors of the present application, a prolongation or shortening of FPrise is also reflected in a prolongation or shortening of QT.

The method according to the invention can be employed, for example, in analysis laboratories as a service provided for doctors, hospitals, pharmaceutical companies, cosmetics companies, or generally in the research and manufacturing industry, in order to gain initial qualitative data on substances which are approved or are to be approved as a medicament or cosmetic product, which occur or are intended to be used as environmental factor or environmental pollutant whose individual effect on a certain subject, patient or patient type is to be determined. In this way, it is possible, in the preliminary stages of human and animal tests, or instead of these tests, to perform an evaluation which not only facilitates the interpretation and appraisal of further studies and investigations but has a decisive input on these.

Further advantages and features will be evident from the following description and from the attached figures.

It will be appreciated that the features mentioned above, and those to be discussed below, can be used not only in the respectively cited combination but also in other combinations or in isolation, without departing from the scope of the present invention.

BRIEF DESCRIPTION OF THE DRAWINGS

Illustrative embodiments of the invention are explained in more detail in the following description in which reference is made to the figures, in which.

DETAILED DESCRIPTION

EXAMPLE 1

Determination of FP Parameters

Heart cells from mouse embryos were cultured in DMEM supplemented with 20% FCS, L-glutamine (2 mmol/L) and nonessential amino acids (all chemicals from Sigma-Aldrich). A drop of the cell suspension ($10^7$ cells/ml) was placed on an MEA produced by the Applicant and having 60 microelectrodes. After attachment of the cells, culture medium was added to give a final volume of 800 µl. After 1 to 3 days in culture, the cells formed a confluent monolayer of multicellular aggregates which showed spontaneous beating activities.

Figure 1:
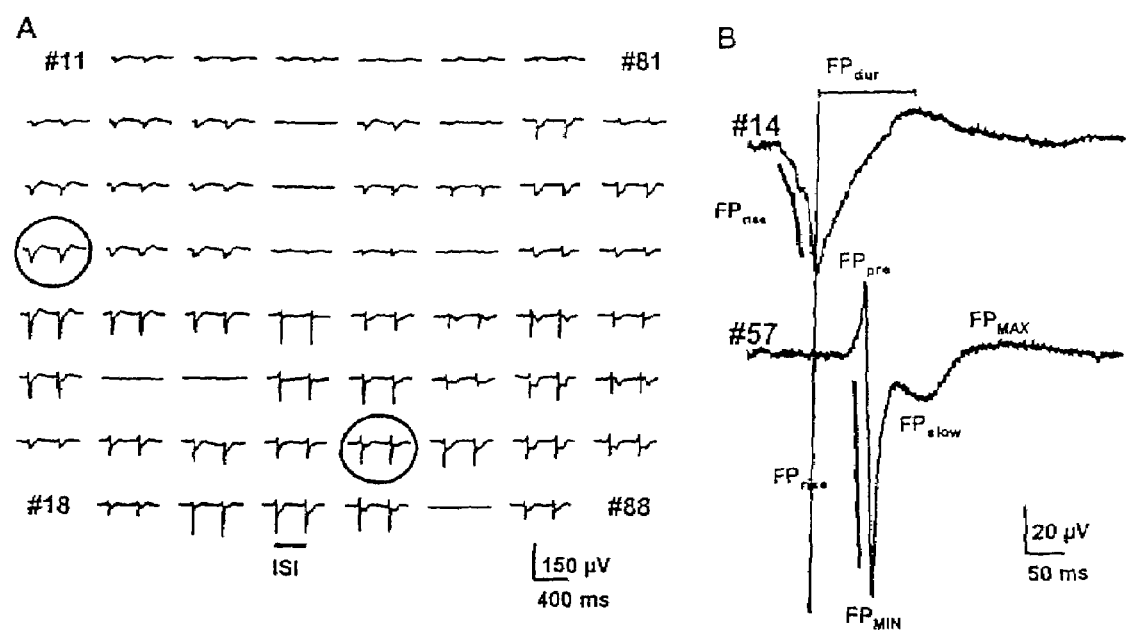
FIG. 1A is a representation of FP wave shapes which were derived using an MEA comprising 60 microelectrodes on a culture of spontaneously beating heart cells.
FIG. 1B is an enlarged representation of two typical FP wave shapes from FIG. 1A, showing inter alia the parameters FPdur and FPrise.

The FP wave shapes measured with the MEA after 4 days in culture are shown in FIG. 1A. Different FP wave shapes were recorded on different microelectrodes, of which two representative examples are shown enlarged in FIG. 1B.

The field potential shows in each case a recurring pattern in the beat rhythm with a first minimum FPmin and a last maximum FPmax, where FPmin and FPmax could in each case be preceded by a further maximum FPpre and FPslow. The time interval between the first minimum and the last maximum is designated as FPdur.

A further parameter of the FP wave shape is the duration of the falling or declining flank in the FP wave shape from the base line to the first minimum FPmin which is characterized by a parameter FPrise. FPrise is calculated as the duration between reaching 10% of FPmin and reaching FPmin.

It was found that FPdur and FPrise are important parameters which can be calculated from the extracellularly derived FP wave shape and which change in a manner comparable to QT upon addition of QT-modifying substances.

EXAMPLE 2

Influence of QT-Modifying Substances on FPdur

In a method comparable to Example 1, ventricular myocytes from chicken embryos were in this case cultured on the MEA. The heart muscle cells were obtained by trypsin digestion of the isolated ventricle of chicken embryos (10-12 days after fertilization). The heart was freed of blood vessels and atria. The cells were cultured in MEM medium supplemented with 10% fetal calf serum (FCS). One to two days before the measurement, the medium was replaced by standard Tyrode solution.

The heart cells were again cultured on the MEA, the derivation and recording time being 10 minutes, which in most cases proved sufficient to permit conclusions to be drawn in this control experiment concerning heart rate and stability of the QT interval.

The standard Tyrode solution was then replaced by a Tyrode solution with 5 μM of a test substance and the change in FPdur was determined. Thereafter, the concentration of the test substance was increased in logarithmic steps. A measurement was now taken every 10 minutes.

In a first test, the substances tested were quinidine and digoxin, the influence of which on QT has long been known.

Quinidine has a QT-prolonging effect and is used as an antiarrhythmic agent; see for example W. B. Campbell, "EKG of the month: QT prolongation induced by quinidine in therapeutic doses", in J. Tenn. Med. Assoc. 1982, 75(5): 340-341.

By contrast, digoxin has a QT-shortening effect and is used in chronic heart insufficiency and to prevent and treat tachycardia; see, for example, Joubert et al., "A correlative study of serum digoxin levels and electrocardiographic measurements", in S. Afr. Med. 1975, 49(29):1177.

In measurements with quinidine, 0.5% DMSO was added to the cell Tyrode since quinidine is not water-soluble. The control experiment was also carried out with DMSO here.

Initial evaluations of these experiments showed that addition of digoxin led to a decrease in FPdur and addition of quinidine led to an increase in FPdur. In these qualitative evaluations, i.e. comparison of data from the respective control experiment and the data derived from addition of the QT-modifying substance, possible changes in the heart rate were taken into account.

Figure 2:
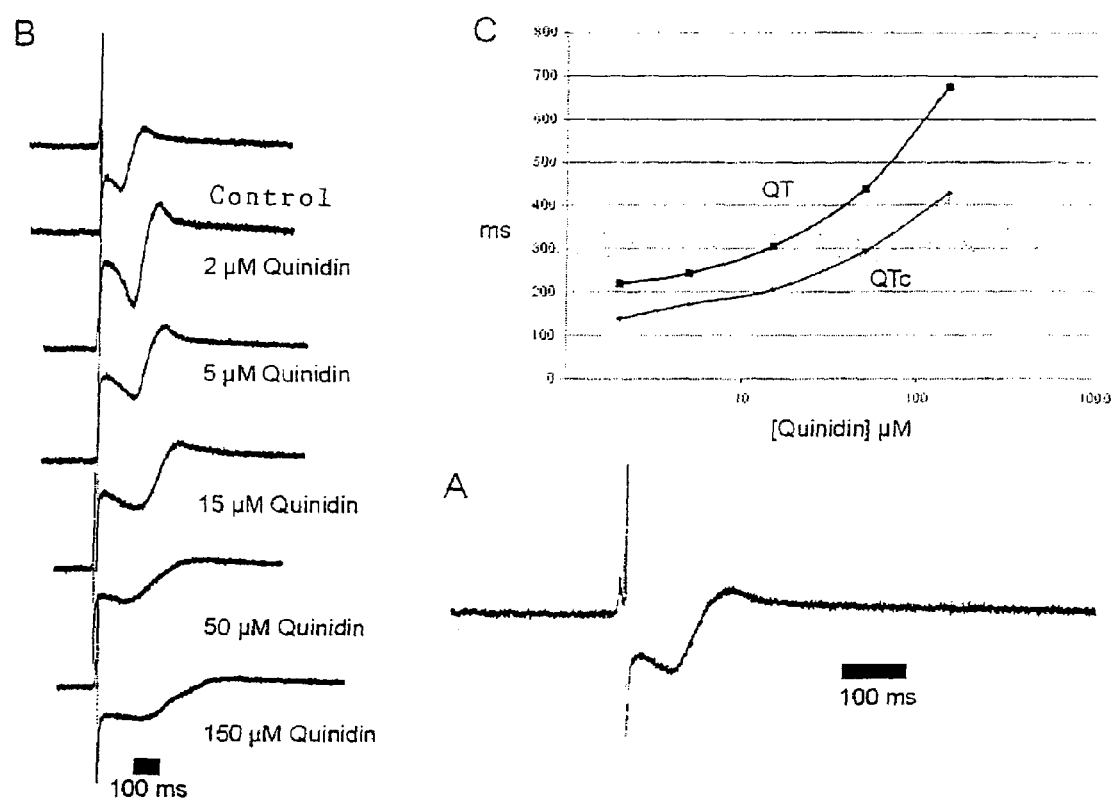
FIG. 2 shows typical measured values obtained, in the test described here, for quinidine at different concentrations.

FIG. 2 shows typical measured values which were determined in the tests described here for quinidine at different concentrations. FIG. 2A shows a typical time course for a field potential measured on MEAs, while FIG. 2B shows field potential courses after addition of the respectively indicated quinidine concentrations for 200 seconds. A QT prolongation increasing with concentration can be clearly seen from the increase in FPdur.

In FIG. 2C, the dose-dependent prolongation is indicated as FPdur (QT) or as FPdur normalized with the heart rate (QTc). For the normalized case, the FPdur value was divided by the square root of the time span (in seconds) between two action potentials.

Figure 3:
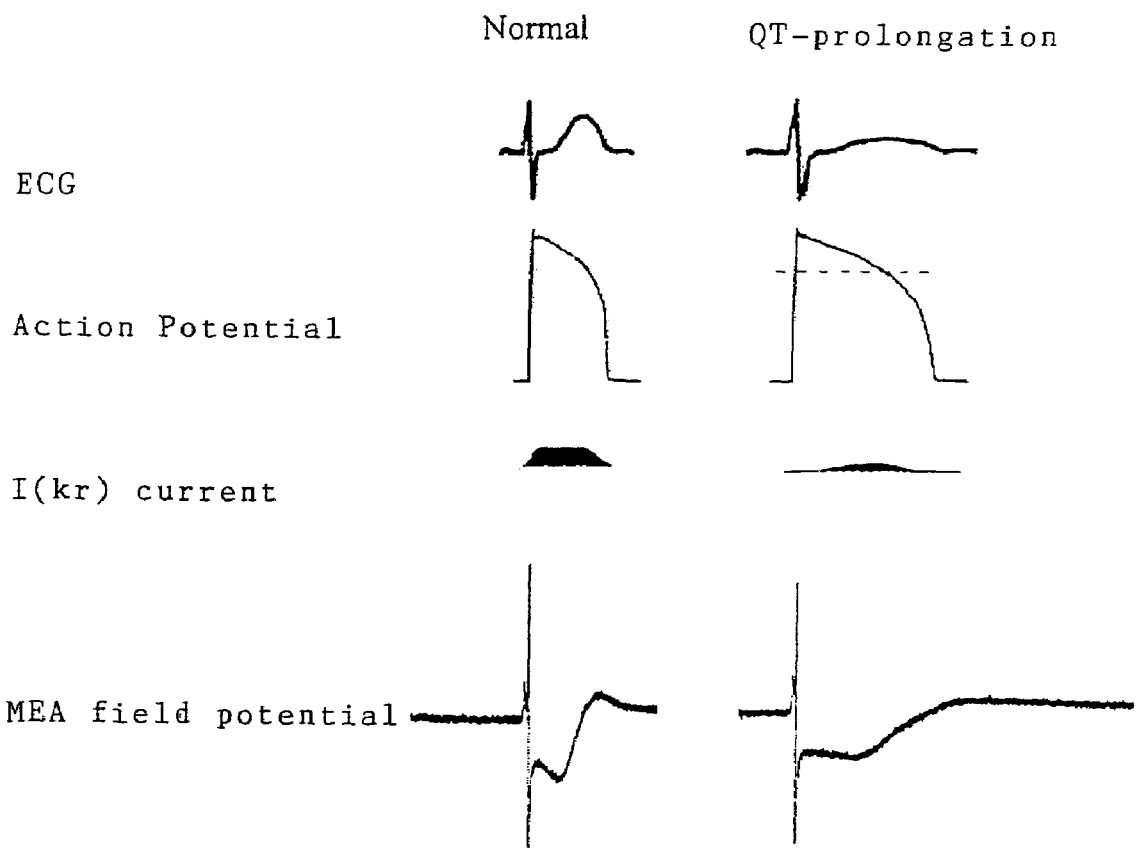
FIG. 3 is a diagrammatic comparison between ECG, action potential, potassium ion current I(Kr) and MEA field potential for ventricular myocytes from chicken embryos without addition (normal) and with addition (QT prolongation) of quinidine.

FIG. 3 shows the diagrammatic comparison between ECG, action potential, potassium ion current I(Kr) and MEA field potential for ventricular myocytes from chicken embryos without addition (normal) and with addition (QT prolongation) of quinidine. It can clearly be seen that the QT prolongation observed in the ECG has its correspondence not only in the measured action potential but also in the field potential, FPdur changes measured by MEAs are therefore a direct measure for QT changes.

Figure 4:
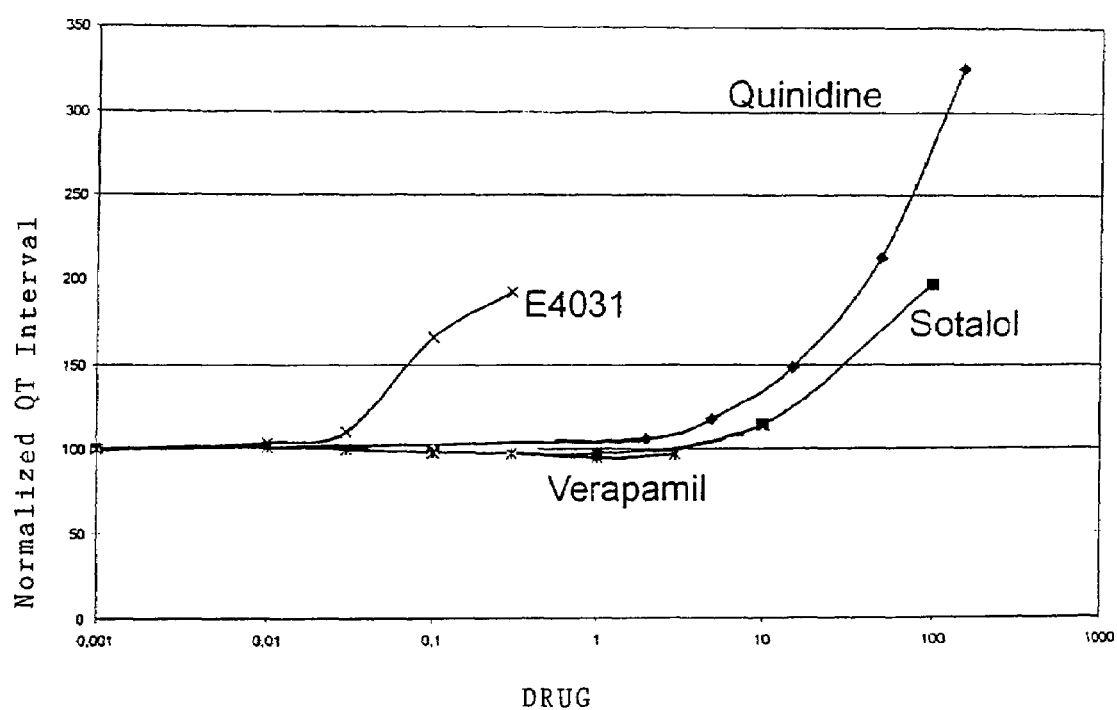
FIG. 4 shows, by way of comparison, the normalized QT interval for four different active substances whose effect on ventricular myocytes from chicken embryos was determined with MEAs.

FIG. 4 shows by comparison the normalized QT interval for four different active substances whose effect on ventricular myocytes from chicken embryos was determined with MEAs.

It has been found that verapamil (5-[N-(3,4-dimethoxyphenylethyl)methylamino]-2-(3,4-dimethoxyphenyl)-2-isopropylvaleronitrile hydrochloride) in the concentration range of from 1 nM to 3 μM has only a very slight effect on QT, although it is known as an antagonist for the L-type calcium channel and blocks potassium channels. Although verapamil would therefore be ruled out as potential medicament in an HERG test, the MEA measurement on spontaneously active heart cells shows that no appreciable QT change is caused.

It follows from this that measurements on only one channel (such as HERG) do not correctly reflect the complex inter-relationships and may lead to false-positive results, whereas this is not the case in MEA measurements (via FPdur).

As a control, FIG. 4 plots the QT changes for the above-discussed quinidine and for E4031 and sotalol, each of which is known to lead to a QT prolongation.

For quinidine, the prolongation of the QT interval in the ECG has been described by a great many authors, and it is recognized by the FDA. Likewise, the FDA confirms an influence of quinidine on the occurrence of tachycardia/torsades de pointes leading to ventricular fibrillation. The QT prolongation was already demonstrated in the 70s. More recent works show an inhibitory effect of quinidine on heterologously expressed HERG channels, as a molecular mediator of QT prolongation.

QT prolongations are already shown in vitro in the MEA system at therapeutic concentrations in the range of 2-7 μM.

Sotalol, (N-[4-[1-hydroxy-2-(isopropylamino)ethyl]phenyl]methanesulfonamidehydrochloride, is also used as an antiarrhythmic agent. QT prolongation and triggering of torsades de pointes have been described in many instances and accepted as side effects. The risk of torsades de pointes is much higher in female patients than in male patients. In the measurements carried out here, a clear prolongation of the action potential was shown (about double). For the known effects of sotalol, reference is made, for example, to: Farkas A., Lepran I., Papp J. G.: Proarrhytmic effects of intravenous quinidine, amiodarone, D-sotalol, and almokalant in the anesthetized rabbit model of torsade de pointes; J. Cardiovasc. Pharmacol. 2002 Feb; 39(2):287-297.

E4031, {4'-[[1-[2-(6-methyl-2-pyridinyl)ethyl-4-piperidinyl]carbonyl]methanesulfonamide, 2HCl}, is not a medication, but a highly selective inhibitor of I(Kr) current. This current is responsible for the repolarization of the ventricular action potential. In terms of molecular biology, the channel through which most of the I(Kr) current flows is referred to as HERG (human ether-a-gogo-related gene). Since HERG channels are often used in heterologous expression systems as in vitro assay for a potential QT prolongation, this substance is of particular importance as a reference.

The sensitivity of the MEA system is also clear from the fact that even submicromolecular concentrations of E4031 lead to inhibition of the I(Kr) current, which is expressed in a prolongation of the ventricular action potential of over 90%. At higher concentrations, the cells no longer have any spontaneous contractions. For the effect of E4031, see for example Webster R., Allan G., Anto-Awuakye K., Harrison A., Kidd T., Leishman D., Walker D.: Pharmacokinetic/pharmacodynamic assessment of the effects of E4031, cisapride, terfenadine and terodiline on monophasic action potential duration in dog, Xenobiotica. 2001 August-September; 31(8-9):633-650.

In so far, the inventors could show the prolongating effect of quinidine, amiodarone (antiarrhythmic agent), terfenadin (antihistaminic agent), astemizol (antihistamic agent), E-4031, cisapride (prokinetic agent), sotalol and fexofenafine (antihistaminic agent) (the latter only at very high concentrations), respectively, on the QT interval. No QT prolongation was found for verapamil (HERG blocker) and ivabradine (IKF blocker, regulates pace maker current).

Further, two substances with so far unknown effect on QT interval have been tested, whereby rilmakalim (IKATP opener) reduced the frequency but did not prolong the field potential, but H1098 had a remarkably prolonged field potential.

The invention claimed is:

1. A method for identifying a test substance that affects the QT interval of the heart, comprising the following steps:
   a) preparation of a culture of spontaneously active heart cells of a vertebrate;
   b) determination of field potential duration (FPdur) and/or field potential rise (FPris),
   wherein FPdur is determined by extracellular measurement or recording of the field potential of the heart cell cultures from step a) and identifying the time interval between the first minimum and last maximum field potential as FPdur,
   wherein FPris is determined by extracellular measurement of recording of the field potential of the heart cell cultures from step a) and determining the duration of the falling flank in the FP wave shape from the zero line to the first minimum as FPris;
   c) addition of the test substance to the culture from step a),
   d) repetition of the measurement from step b), and
   e) comparison of data from step b) and step d), wherein a change in the FPdur and/or the FPris in the presence of the test substance identifies said test substance as one that affects the QT interval of the heart and the absence of a change in the FPdur and/or the FPris in the presence of the substance identifies said test substance as one that does not affect the QT interval of the heart.

2. The method of claim 1, wherein the effect on the FPdur is a prolongation or a shortening of the FPdur.

3. The method of claim 2, wherein said prolongation or shortening of the FPdur corresponds to a prolongation or shortening of the QT interval.

4. The method of claim 1, wherein the effect on the FPris is a prolongation or a shortening of the FPris.

5. The method of claim 4, wherein said prolongation or shortening of the FPris corresponds to a prolongation or shortening of the QT interval.

6. The method of claim 1, wherein said test substance is an approved medicament, a medicament for approval, a human medicine, a veterinary medicine, an environmental factor, a cosmetic product, or an environmental pollutant.

7. The method of claim 1, wherein said heart cell culture comprises individual heart cells, aggregates of heart cells, or tissue composites of heart cells.

8. The method of claim 1, wherein said heart cell culture comprises heart cells from biopsies or clinical material, heart cells from stem cells, or heart cell lines.

9. The method of claim 1, wherein said field potential is determined using a multi-electrode array (MEA).

10. The method of claim 1, further comprising a plurality of heart cell cultures.

11. The method of claim 10, wherein said plurality of cultures is on a support plate.

12. The method of claim 11, wherein said support plate comprises a plurality of well or microcuvettes, wherein each well or microcuvette holds a heart cell culture.

13. The method of claim 12, wherein at least one measurement electrode is provided for recording of field potential in each well or microcuvette.

14. The method of claim 1, wherein said vertebrate is a mammal.

15. The method of claim 14, wherein said mammal is a livestock animal, a domestic animal, or a human.

* * * * *